(12) United States Patent
Schena

(10) Patent No.: US 8,377,045 B2
(45) Date of Patent: Feb. 19, 2013

(54) EXTENDABLE SUCTION SURFACE FOR BRACING MEDIAL DEVICES DURING ROBOTICALLY ASSISTED MEDICAL PROCEDURES

(75) Inventor: Bruce Schena, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 838 days.

(21) Appl. No.: 11/762,231

(22) Filed: Jun. 13, 2007

(65) Prior Publication Data

US 2007/0287884 A1  Dec. 13, 2007

Related U.S. Application Data

(60) Provisional application No. 60/813,198, filed on Jun. 13, 2006.

(51) Int. Cl.
*A61B 17/00* (2006.01)
(52) U.S. Cl. .......................................................... 606/1
(58) Field of Classification Search ............... 606/130, 606/148, 150, 201, 1, 107, 166, 121–122, 606/119, 123; 600/156, 201, 204, 214, 216, 600/217, 235, 104, 205, 215; 607/119, 127, 607/116; 901/40; 294/64.1
See application file for complete search history.

(56) References Cited

U.S. PATENT DOCUMENTS

| | | | |
|---|---|---|---|
| 4,723,940 A * | 2/1988 | Wiegerinck | 604/115 |
| 5,297,536 A | 3/1994 | Wilk | |
| 5,382,231 A | 1/1995 | Shlain | |
| 5,458,131 A | 10/1995 | Wilk | |
| 5,484,391 A * | 1/1996 | Buckman et al. | 601/135 |
| 6,007,523 A * | 12/1999 | Mangosong | 604/284 |
| 6,063,021 A * | 5/2000 | Hossain et al. | 600/37 |
| 6,786,898 B2 * | 9/2004 | Guenst | 606/1 |
| 6,890,295 B2 | 5/2005 | Michels et al. | |
| 7,186,262 B2 | 3/2007 | Saadat | |
| 7,250,028 B2 * | 7/2007 | Julian et al. | 600/229 |
| 2001/0023311 A1 * | 9/2001 | Snow | 600/37 |
| 2002/0177847 A1 * | 11/2002 | Long | 606/46 |
| 2003/0171664 A1 * | 9/2003 | Wendlandt | 600/407 |
| 2003/0176880 A1 * | 9/2003 | Long et al. | 606/167 |
| 2003/0216613 A1 | 11/2003 | Suzuki et al. | |
| 2004/0087831 A1 * | 5/2004 | Michels et al. | 600/114 |
| 2004/0088035 A1 * | 5/2004 | Guenst et al. | 607/131 |
| 2006/0200002 A1 * | 9/2006 | Guenst | 600/201 |

OTHER PUBLICATIONS

Vertut, Jean and Philippe Coiffet, *Teleoperation and Robotics: Evolution and Development*, English translation Prentice-Hall, Inc., Inglewood Cliffs, NJ, USA, 1986.

* cited by examiner

*Primary Examiner* — Ryan Severson
*Assistant Examiner* — David Eastwood

(57) ABSTRACT

Medical devices robotically manipulated by a medical robotic system for performing a medical procedure on a patient are bundled together as a bundled unit and inserted into the patient through a single entry port. Bracing of the bundled unit at a surgical site is performed by extending a suction surface disposed at a distal end of the bundled unit towards a bracing surface at the surgical site and applying a suction force between the suction surface and the bracing surface. The suction surface is ring-shaped with holes distributed about the ring so that controllably extendable and retractable tubes coupled at distal ends to the holes provide suction to the suction surface when coupled at proximal ends to a vacuum source.

9 Claims, 7 Drawing Sheets

EXTENDABLE SUCTION SURFACE FOR BRACING MEDIAL DEVICES DURING ROBOTICALLY ASSISTED MEDICAL PROCEDURES

CROSS REFERENCE TO RELATED APPLICATIONS

This application claims priority to U.S. provisional application Ser. No. 60/813,198 filed Jun. 13, 2006, which is incorporated herein by reference.

FIELD OF THE INVENTION

The present invention generally relates to the bracing of surgical tools during the performance of medical procedures using robotic systems and in particular, to an extendable suction surface for bracing medical devices during robotically assisted medical procedures.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

Examples of medical robotic systems include the da Vinci® Surgical System and the da Vinci® S™ Surgical System from Intuitive Surgical, Inc., of Sunnyvale, Calif. Each of these systems includes a surgeon's consoler a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery.

During the performance of a medical procedure, it may be useful to brace the surgical instruments used in performing the medical procedure and/or an image capturing device used for viewing the medical procedure so as to be restricted or otherwise constrained in their movement relative to an anatomic structure at a surgical site. Without such bracing, precise positioning of the end effectors of the surgical tools relative to the anatomical structure may be difficult to control. For example, external forces may be exerted against the end effectors causing them to move. Also, the target tissue being subjected to a medical procedure may move due to its natural movement, or movement of adjacent organs, or the flow of blood through adjacent veins or arteries.

When performing certain medical procedures, it is advantageous to insert the surgical instruments and the image capturing device as a bundled unit through a single port, such as a natural body orifice or a minimally invasive incision, in the patient. In such a bundled unit, however, mechanical coupling between the bundled components may cause undesirable movement of one component as a result of an external force being exerted against another. Thus, bracing of the entire bundled unit may be advantageous for better relative position control of its individual surgical instruments.

OBJECTS AND SUMMARY OF THE INVENTION

Accordingly, one object of one or more aspects of the present invention is a method and apparatus for bracing a bundled unit of medical devices at a surgical site within a patient.

Another object of one or more aspects of the present invention is a method and apparatus for removing selected tissue from a surgical site after the performance of a medical procedure targeting the tissue.

These and additional objects are accomplished by the various aspects of the present invention, wherein briefly stated, one aspect is a medical unit comprising: an elongate structure having a first lumen; a first surgical tool inserted within the first lumen; and a controllably extendable and retractable suction surface disposed on a distal end of the elongate structure, wherein the suction surface is couplable to a vacuum source so that at least one opening of the suction surface is provided with a suction force capable of bracing the elongate structure against an anatomic structure when positioned so as to be in contact with the anatomic structure.

Another aspect is a method for performing a medical procedure at a surgical site within a patient using a bundled unit of medical devices, comprising: robotically guiding the bundled unit of medical devices through a single port entry within the patient to the surgical site; robotically extending a suction surface disposed at a distal end of the bundled unit towards a bracing surface; bracing the bundled unit against the bracing surface by applying a suction force between the suction surface and the bracing surface; and robotically performing the medical procedure using the bundled unit of medical devices.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
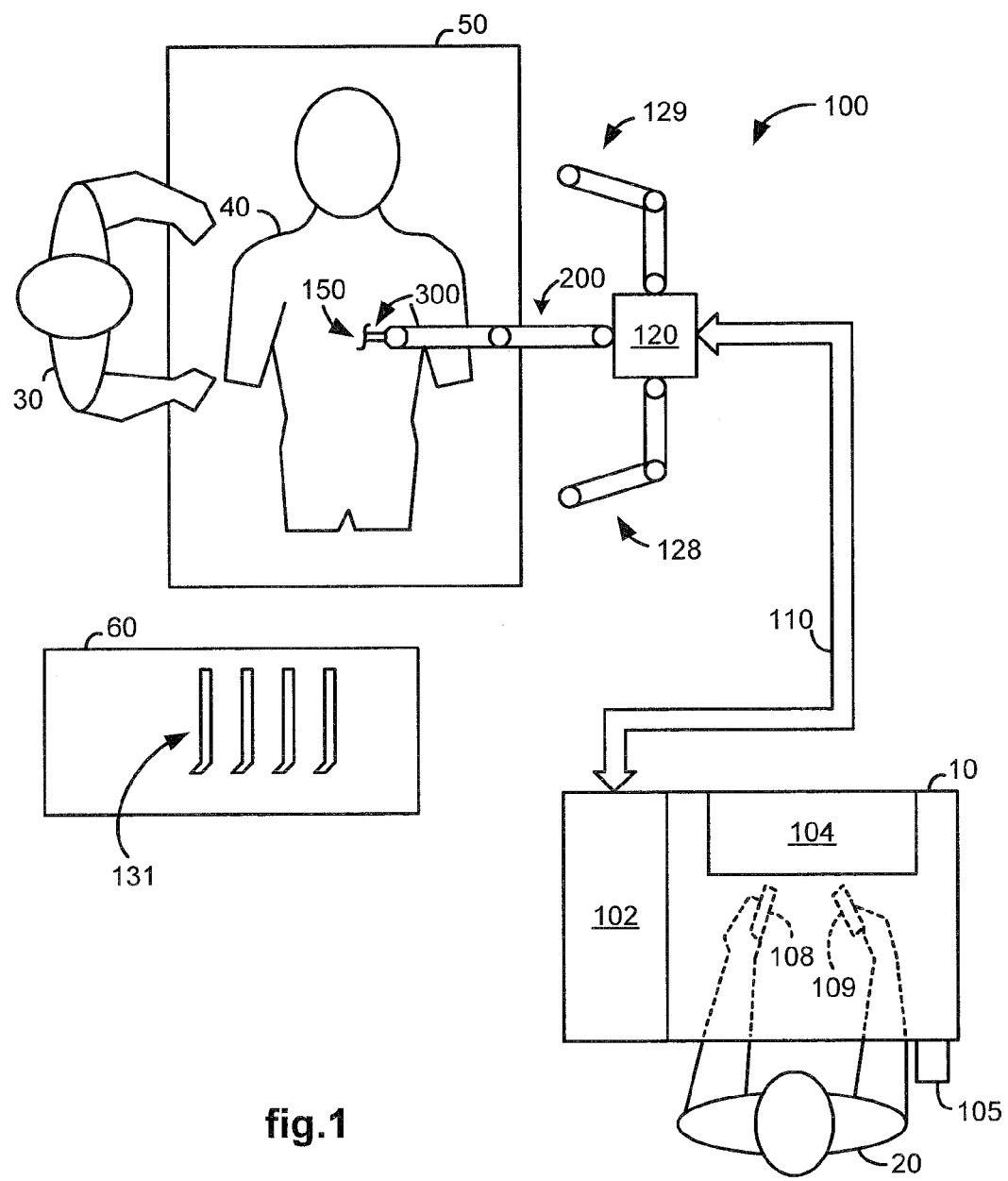
FIG. 1 illustrates a top view of an operating room employing a medical robotic system with a bundled unit of medical devices utilizing aspects of the present invention.

FIG. 1 illustrates, as an example, a top view of an operating room in which a medical robotic system 100 is being utilized by a Surgeon 20 for performing a medical procedure on a Patient 40 who is lying down on an operating table 50. One or more Assistants 30 may be positioned near the Patient 40 to assist in the procedure while the Surgeon 20 performs the procedure teleoperatively by manipulating control devices 108, 109 on a surgeon console 10.

In the present example, a bundled unit 300 of medical devices is inserted through a single entry port 150 into the Patient 40. Although the entry port 150 is a minimally invasive incision in the present example, in the performance of other medical procedures, it may instead be a natural body orifice. The bundled unit 300 is held and manipulated by a robotic arm assembly 200. Although only one robotic arm assembly is used in the present example, the medical robotic system 100 is equipped with additional robotic arm assemblies 128, 129 which are swung out of the way during the performance of the present medical procedure, because they are not being used.

The console 10 includes a 3-D monitor 104 for displaying a 3-D image of a surgical site to the Surgeon, left and right manipulatable control devices 108, 109, a foot pedal 105, and a processor 102. The control devices 108, 109 may include any one or more of a variety of input devices such as joysticks, gloves, trigger-guns, hand-operated controllers, or the like. The processor 102 may be a dedicated computer integrated into the console 10 or positioned next or near to it, or it may comprise a number of processing or controller components that are distributed in a distributed processing fashion throughout the system 100.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
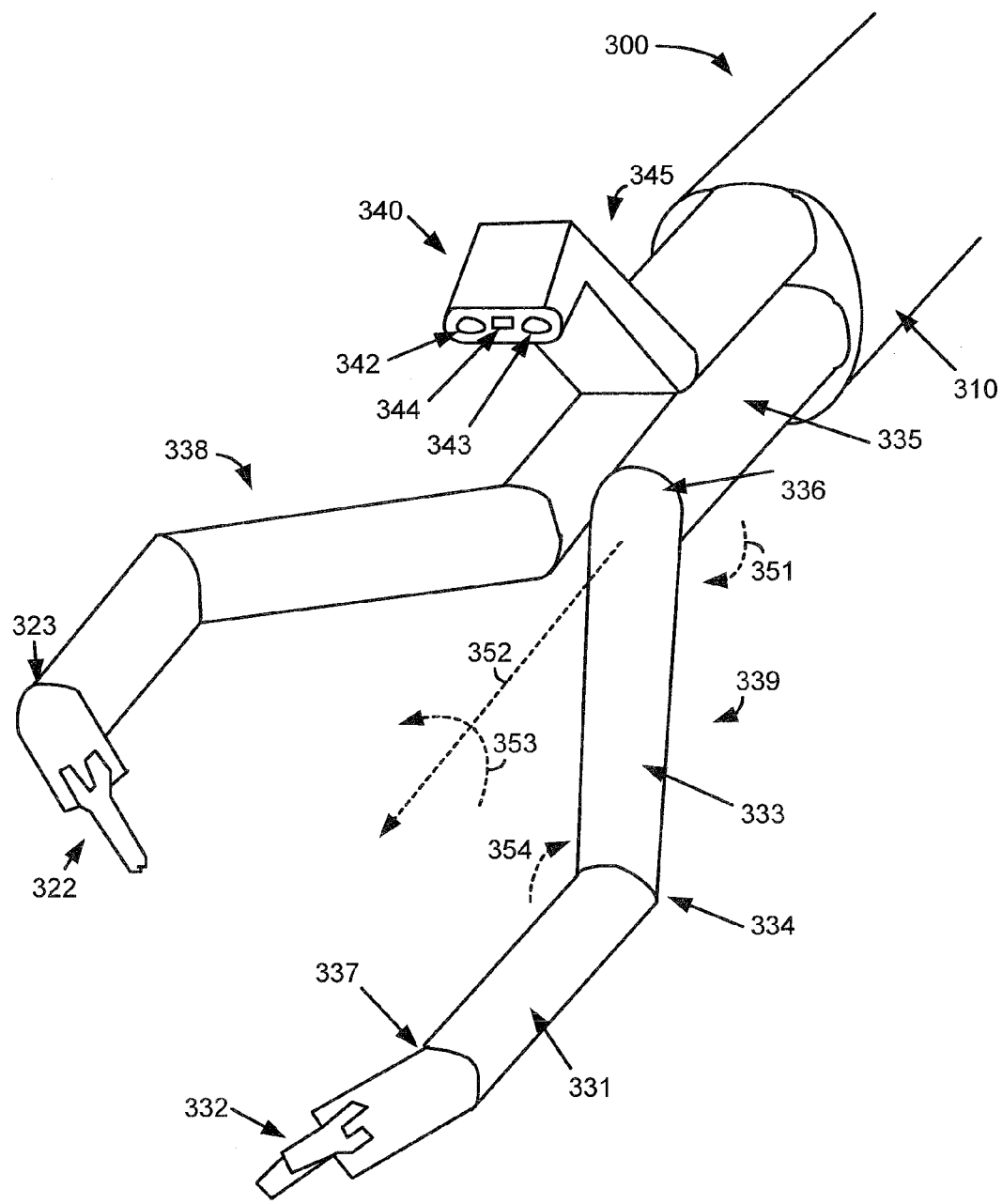
FIG. 3 illustrates a perspective view of a distal end of a bundled unit of medical devices utilizing aspects of the present invention.

As shown in FIG. 3, the bundled unit 300 may include two surgical instruments or tools 338, 339 and an image capturing device 340. Each of the surgical tools 338, 339 is associated with one of the control devices 108, 109. The Surgeon performs a medical procedure by manipulating the control devices 108, 109 so that the processor 102 causes corresponding movement of their respectively associated surgical tools 338, 339, while the Surgeon views the surgical site in 3-D on the console monitor 104 as it is captured by the image capturing device 140.

Preferably, control devices 108, 109 will be provided with at least the same degrees of freedom as their associated tools 338, 339 to provide the Surgeon with telepresence, or the perception that the control devices 108, 109 are integral with the tools 338, 339 so that the Surgeon has a strong sense of directly controlling the tools 338, 339.

Preferably, the monitor 104 is positioned near the Surgeon's hands so that it will display a projected image that is oriented so that the Surgeon feels that he or she is actually looking directly down onto the operating site. To that end, images of the tools 338, 339 preferably appear to be located substantially where the Surgeon's hands are located.

In addition, the real-time image is preferably projected into a perspective image such that the Surgeon can manipulate the end effectors 322, 332 of the tools 338, 339 through their corresponding control devices 108, 109 as if viewing the workspace in substantially true presence. By true presence, it is meant that the presentation of an image is a true perspective image simulating the viewpoint of an operator that is physically manipulating the tools 338, 339. Thus, the processor 102 transforms the coordinates of the tools 338, 339 to a perceived position so that the perspective image is the image that one would see if the image capturing device 140 was located directly behind the tools 338, 339.

The processor 102 performs various functions in the system 100. One important function that it performs is to translate and transfer the mechanical motion of control devices 108, 109 to the robotic arm assembly 200 through control signals over bus 110 so that the Surgeon can effectively manipulate the tools 338, 339.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system such as in printed circuit boards installed in the patient side cart 120 and/or the robotic arm assemblies 128, 129, 200, as well as, or alternatively to, the console 10.

For additional details on the construction and operation of various aspects of a medical robotic system such as described herein, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by reference.

Figure 2:
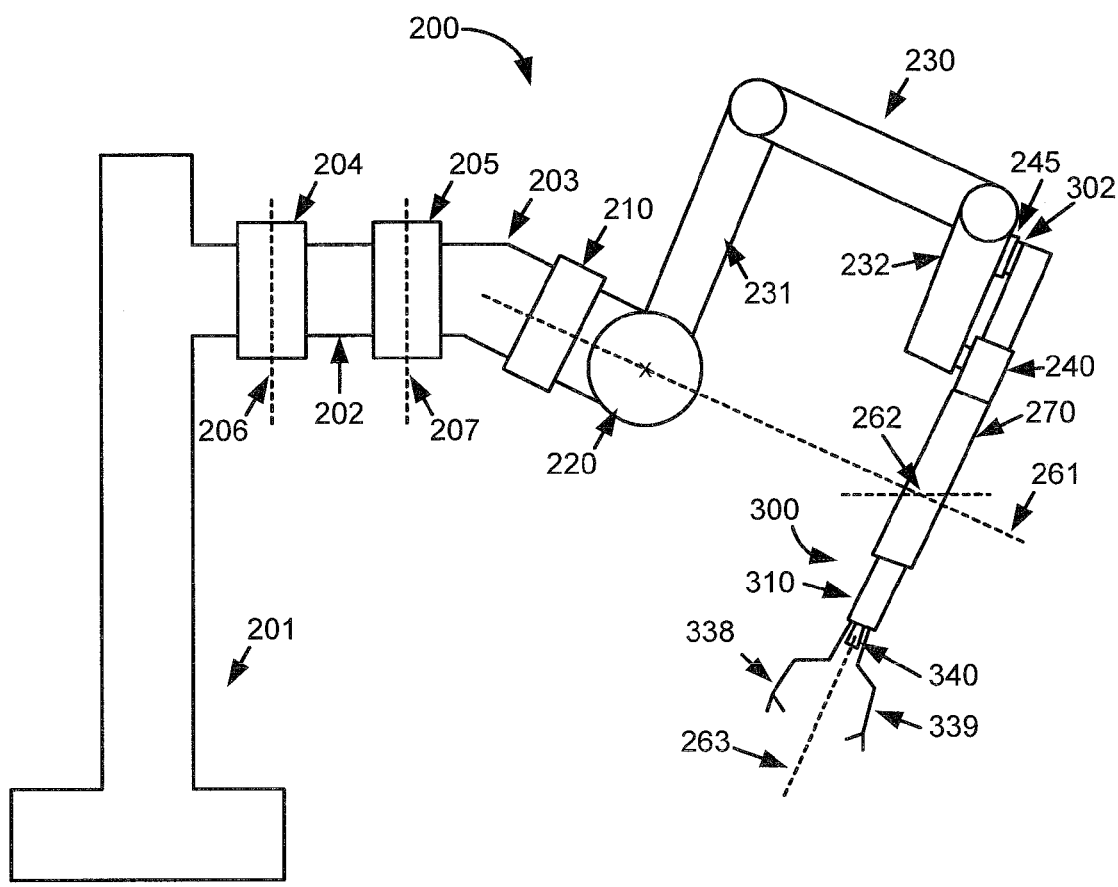
FIG. 2 illustrates a side view of a simplified robotic arm assembly holding a bundled unit of medical devices utilizing aspects of the present invention.

FIG. 2 illustrates, as an example, a simplified side view (not necessarily in proportion or complete) of the robotic arm assembly 200 which is holding the bundled unit 300 of medical devices. A tool guide 270 is inserted through the minimally invasive incision 150 in the Patient, and coupled to the robotic arm assembly 200 by a guide holder 240. The bundled unit 300 may then be inserted into the Patient through the tool guide 270. The robotic arm assembly 200 is mechanically supported by a base 201 of the patient side cart 120.

Links 202, 203 are coupled together and to the base 201 through horizontal setup joints 204, 205. The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207.

Although only two links and two setup joints are shown in this example, more or fewer of each may be used as appropriate in this and other robotic arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The robotic arm assembly 200 also includes two active joints and a number of gears driven by motors. A yaw joint 210 allows arm section 230 to rotate around an axis 261, and a pitch joint 220 allows arm section 230 to rotate about an axis perpendicular to that of axis 261 and orthogonal to the plane of the drawing. An interface 302 comprises mating parts on the carriage 245 and the proximal end of the bundled unit 300 such as motor driven gears that actuate movement of the surgical tools 338, 339, image capturing unit 340, and one or more individually controllable suction surfaces (e.g., suction surface 500 in FIG. 5 or suction surfaces 801, 802 in FIG. 8) through conventional joints, cable and pulley systems.

The arm section 230 is configured so that sections 231, 232 are always parallel to each other as the pitch joint 220 is rotated by its motor. As a consequence, the bundled unit 300 may be controllably moved by driving the yaw and pitch motors so as to pivot about the pivot point 262, which is generally located through manual positioning of the setup joints 204, 205 so as to be at the point of entry into the Patient. In addition, the bundled unit 300 is coupled to a carriage 245 on the arm section 230 which in turn is coupled to a linear drive mechanism to extend or retract the bundled unit 300 along its insertion axis 263.

Although each of the yaw joint 210, pitch joint 220 and motor driven gears in the carriage 245 is controlled by an individual joint or gear controller, the controllers may be controlled by a common master/slave control system so that the medical devices of the bundled unit 300 may be controlled through user (e.g., Surgeon or operator) manipulation of its associated control device.

FIG. 3 illustrates, as an example, a perspective view of a distal end of the bundled unit 300. The bundled unit 300 includes removable surgical tools 338, 339 for performing a medical procedure and a removable image capturing unit 340 for viewing the procedure at a surgical site within a patient. Each of the tools 338, 339 and image capturing unit 340 extends through a separate lumen formed in an inner core of the bundled unit 300. Replacement of one or both of the surgical tools 338, 339 during or in preparation for performing a medical procedure may then be accomplished by the Assistant removing the tool that is no longer needed from its lumen and replacing it with a substitute tool 131 from a tray 60 by inserting the substitute tool 131 in the vacated lumen. Alternatively, if unused lumens are available, an additional tool may be inserted through one of those available lumens without removing any other tools already in place.

The image capturing unit 340 preferably includes a stereoscopic pair of cameras 342, 343 for three-dimensional imaging of the surgical site and an illuminating device 344 such as a light emitting diode (LED) or a fiber optics bundle carrying light from an external source, to enhance visibility of objects in the captured images. Auxiliary image capturing units, such as an ultrasound probe, may also be provided in available lumens of the bundled unit 300 for "seeing" into anatomic structures for surgical or diagnostic purposes.

In some embodiments, an overtube 310 is also included in the bundled unit 300 for protecting its inner core and the medical devices (i.e., surgical tools and image capturing units) inserted therethrough. The overtube 310 may be rigid. Alternatively, it may be formed of flexible material or comprise actively and/or passively bendable sections so that the bundled unit 300 may conform to the shapes of body lumens as it moves therethrough to a surgical site within a patient.

The surgical tools 338, 339 each have a controllably extendable, rotatable, and bendable arm to which their respective end effectors 322, 332 are coupled to by wrist mechanisms 323, 337. For example, the arm of the surgical tool 339 comprises three links 331, 333, 335 coupled by distal joints 334, 336. The proximal link 335 is controllably extendable and retractable along an insertion axis 352 (which is preferably parallel to the insertion axis 263 of the single-port device 300), and is controllably rotatable (as shown by rotation angle 353) about the insertion axis 352. The middle link 333, on the other hand, is controllably bendable by distal joint 336 relative to the link 335 (as shown by bend angle 351), and the distal link 331 is coupled to the links 333, 335 and bendable by distal joint 334 so that its bend angle 354 is in an opposite direction as that of the link 333 and consequently, keeps links 331, 335 in parallel alignment.

The arm of the surgical tool 338 is similarly constructed as that of the surgical tool 339. Additional details for one example of the wrist mechanisms 323, 337 are provided in commonly owned U.S. Pat. No. 6,817,974 "Surgical Tool Having Positively Positionable Tendon-Actuated Multi-Disk Wrist Joint," which is incorporated herein by this reference.

The image capturing unit 340 also has a controllably extendable, rotatable, and bendable arm 345 that facilitates at least insertion/retraction of the image capturing unit 340 along its insertion axis (which may be parallel to the insertion axis 263 of the single-port device 300) and pitch motion in order to achieve a sufficient elevation of the image capturing device 340 "above" the surgical tools 338, 339 so as to properly view them during a surgical procedure. Additional degrees of freedom, such as roll angular movement of the image capturing device 340 about its insertion axis, may also be provided in order to facilitate additional positioning and orientation capabilities for the image capturing device 340. For enhanced maneuverability, the image capturing arm 345 may also be bendable such as the controllably bendable, rotatable, and extendable arms of the surgical tools 338, 339.

Figure 4:
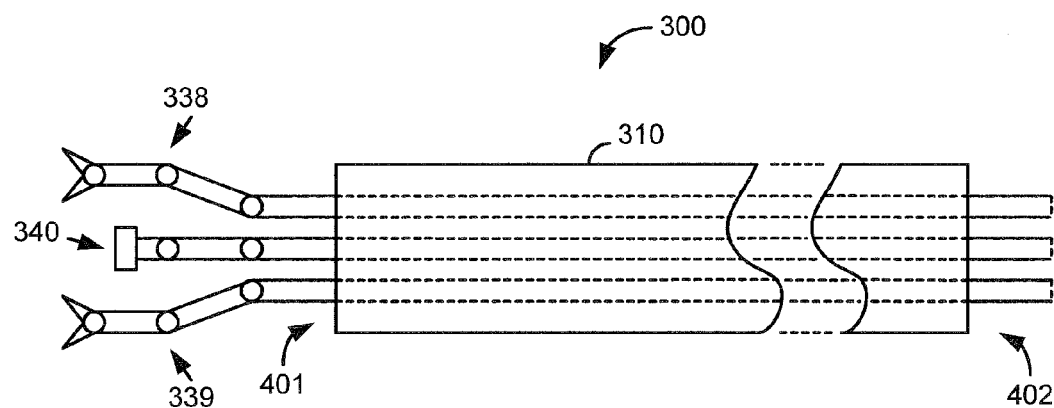
FIGS. 4-5 illustrate simplified top and cross-sectional views of a bundled unit of medical devices that has an extendable suction surface for bracing the bundled unit against an anatomic structure in a patient's body, utilizing aspects of the present invention.
Figure 5:
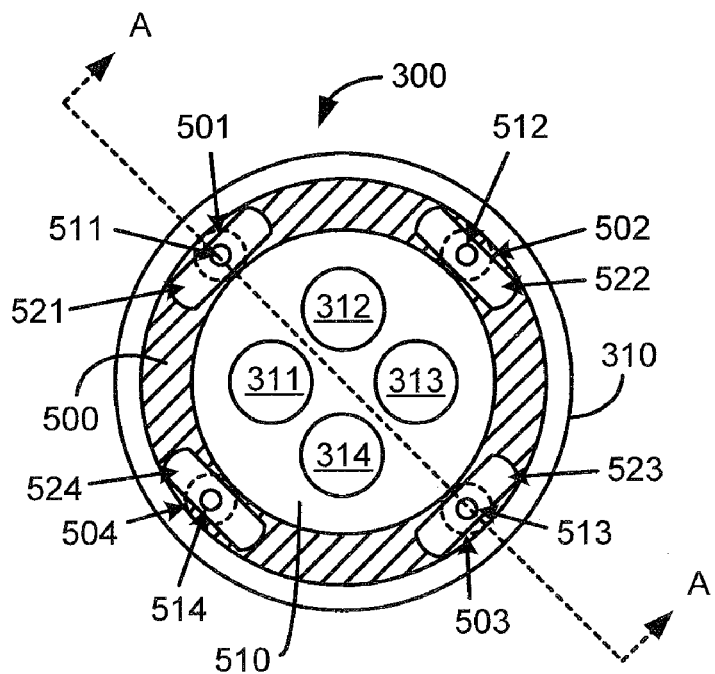

FIG. 4 illustrates, as an example, a simplified top view of the bundled unit 300 with surgical tools 338, 339 and an image capturing device 340 extending out of the distal end 401 of the bundled unit 300, and FIG. 5 illustrates, as an example, a distal end view of the bundled unit 300 with the surgical tools 338, 339 and image capturing device 340 removed so that other components at the distal end 400 of the bundled unit 300 may be better seen and described. The bundled unit 300 includes an overtube 310 which has a plurality of lumens 311~314 extending within its core 510 and between its distal and proximal ends. In an exemplary configuration, the surgical tools 338, 339 are inserted in lumens 311, 313, and the image capturing device 340 is inserted in lumen 312. Lumen 314 is available in this case for insertion of another medical device such as an auxiliary image capturing device or other surgical tool useful for performing a medical procedure on the Patient. At the proximal end 402 of the bundled unit 300, the surgical tools 338, 339 and image capturing device 340 attach to the interface 302 which interfaces the robotic arm 200 to these medical devices so as to facilitate Surgeon manipulation of the medical devices using, for example, the input devices 108, 109 on the Surgeon console 10.

A suction surface 500 in the shape of a ring is disposed on the distal end 401 of the bundled unit 300. A plurality of suction plenums 521~524 are formed in the suction surface 500, and a corresponding plurality of tubes 501~504 having inner conduits 511~514 are coupled on their distal ends to the plenums 521~524 and couplable on their proximal ends to a vacuum source (not shown) so that suction forces may be applied on the suction surface 500 through openings of the plenums 521~524. In addition to providing suction on the distal side of the suction surface 500, the tubes 501~504 are also robotically manipulatable through operator input (such as foot pedal 105, a button on one of the control inputs 108, 109, a graphical user interface displayed on the monitor 104, voice activation, or other input means) so that the suction surface 500 is controllably extendable away from and retractable back to the distal end 401 of the bundled unit 300. Preferably, the suction forces may be turned on and off by the Surgeon or Assistant turning a valve on the vacuum source (not shown), so as to effectively couple and decouple the vacuum source to the tubes 501~504.

Figure 6:
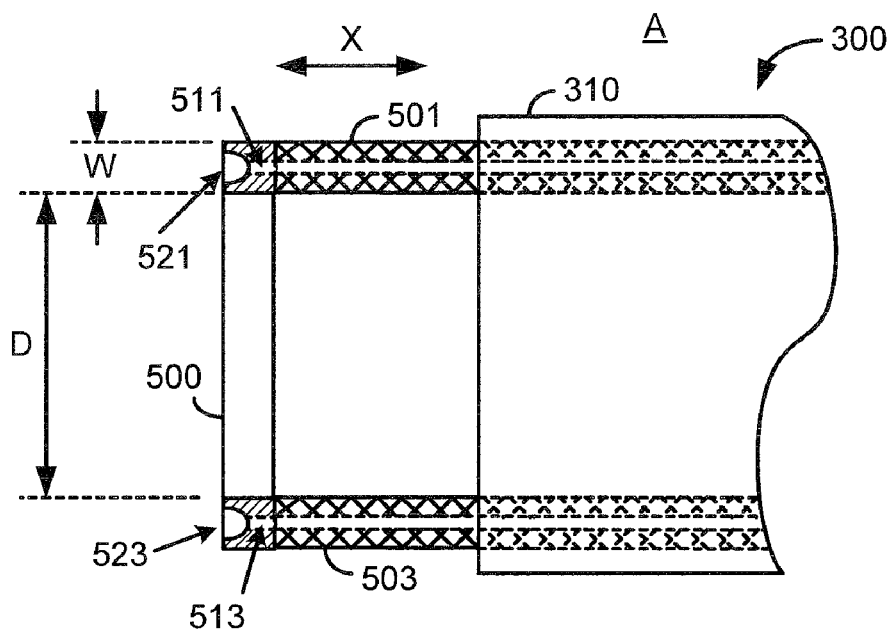
FIG. 6 illustrates a simplified cut-out view of a bundled unit of medical devices with an extendable suction surface in an extended position, utilizing aspects of the present invention.

FIG. 6 illustrates, as an example, a simplified cut-out view of the bundled unit 300 along cut "A" as shown in FIG. 5 with the suction surface 500 in an extended position away from the distal end 401 of the bundled unit 300. From this cut-out view, cross-sections of tubes 501, 503 are shown as having their distal ends coupled to the suction surface 500 in such a fashion that the inner conduits 511, 513 of the tubes 501, 503 are aligned with holes of their corresponding plenums 521, 523 of the suction surface 500 so that a vacuum source (not shown) coupled at their proximal ends may generate suction forces on the suction surface 500 through the plenums 521, 523. Although not shown in this figure, tubes 502, 504 are similarly coupled to the suction surface 500 at their distal ends so that their inner conduits 512, 514 are respectively aligned with holes of their corresponding plenums 522, 524 of the suction surface 500, and couplable at their proximal ends to the vacuum source (not shown).

Each of the tubes 501~504 is also coupled at its proximal end to the interface 302, which interfaces the bundled unit 300 to the robotic arm 200 of the robotic system 100 as shown in FIG. 2, so that the tubes 501~504 may be robotically manipulated by the operator to move in unison in the "X" direction so as to either extend away from the distal end 401 of the bundled unit 300 or retract back to the distal end 401 and consequently, extend and retract the suction surface 500 away and back towards the distal end 401 of the bundled unit 300.

The width "W" of the ring-shaped suction surface 500 preferably results in an outer diameter that is not much larger than the inner diameter "D" of the ring-shaped suction surface 500. Thus, when the anatomic structure to which the suction surface 500 is being braced is tissue targeted for processing during a medical procedure, the suction surface 500 minimizes the amount of target tissue that it covers up and consequently, is inaccessible for treatment.

Figure 7:
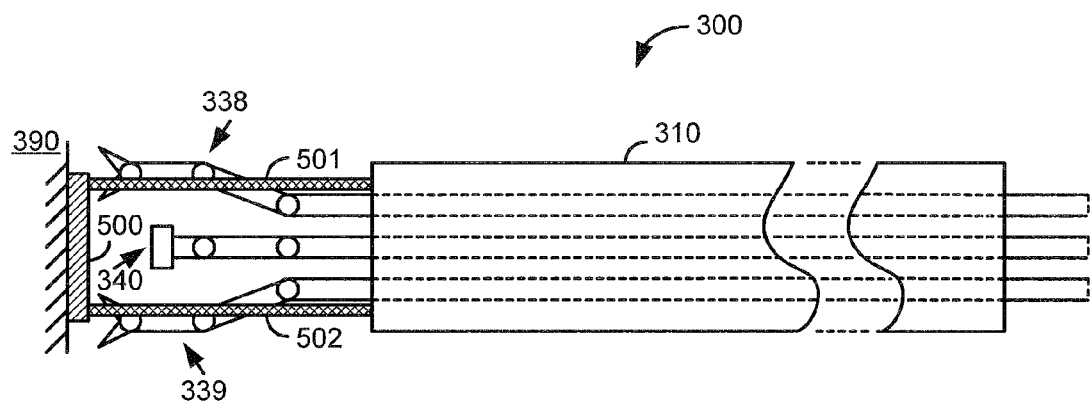
FIG. 7 illustrate simplified top view of a bundled unit of medical devices with an extendable suction surface in an extended position and bracing the bundled unit against an anatomic structure, utilizing aspects of the present invention.

As shown in FIG. 7, when the suction surface 500 is extended out to contact a bracing surface such as the surface of an anatomic structure 390 and suction is applied through vacuums created in the plenums 521~524, the bundled unit 300 is effectively held in place (i.e., braced) relative to the anatomic structure 390. Referring to FIG. 5, the plenums 521~524 are distributed around the suction surface 500 so as to evenly apply suction to the bracing surface. The plenums 521~524 are also offset relative to the lumens 311~314 so as to allow linkage arms of surgical tools 338, 339 inserted in the lumens 311, 313 to bend "elbows out" without the tubes 501~504 preventing them from doing so. In addition, the linkage arm of image capturing device 340 inserted in lumen 312 is also allowed to bend in a "crane configuration" above the bundled unit 300 so as to view the surgical tools 338, 339 without the tubes 501~504 preventing it from doing so. Thus, when the anatomic structure 390 is target tissue being treated by the Surgeon during a medical procedure, end effectors 322, 332 of the surgical tools 338, 339 may freely operate on the target tissue both inside and outside of the inner core of the ring-shaped suction surface 500.

The tubes 501~504 may be rigid so as to resist relative movement between the suction surface 500 and the anatomic structure to which it is being braced, or they may be semi-rigid so as to allow some movement between the suction surface 500 and the anatomic structure. Contact sensors (not shown) may be disposed on the distal side of the suction surface 500 so that contact with an anatomic structure can be detected. Alternatively, such contact may be determined visually using images captured by the image capturing device 340, or physically using force or torque sensors coupled to actuators (not shown) which drive the extension and retraction of the tubes 501~504. A suction force may be applied to holes 511~514 either before or after contact is detected, by, for example, opening a valve connecting the vacuum source (not shown) to the proximal ends of the tubes 501~504.

Figure 8:
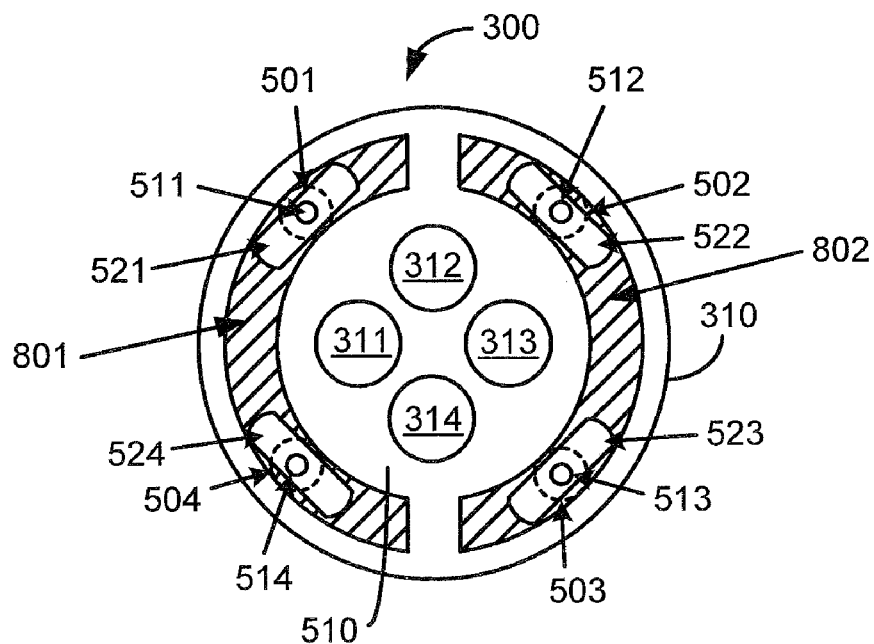
FIG. 8 illustrates a cross-section view of a bundled unit of medical devices that has two extendable suction surfaces for bracing the bundled unit against an anatomic structure in a patient's body, utilizing aspects of the present invention.

As may be readily appreciated, the shape of the suction surface is not necessarily limited to being ring-shaped. For example, it may be a square, rectangular, ellipsoidal, or any other polygonal shape with a suitably hollowed out central portion. It may also be a concave structure such as a C-shape, L-shape, or U-shape. In addition, the number of suction surfaces employed at the distal end of the bundled unit 300 is not necessarily limited to any specific number. For example, the ring-shaped suction surface 500 may be split into two C-shaped suction surfaces 801, 802 as shown in FIG. 8, in which each of the separate suction surfaces 801, 802 may be individually controllable or controlled in a coupled manner so as to be extendable away from and/or retractable back to the distal end of the bundled unit 300.

Figure 9:
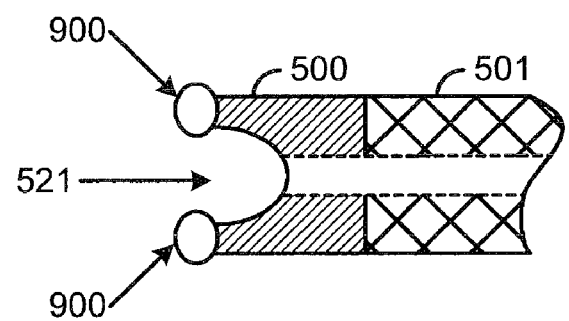
FIG. 9 illustrates a simplified cut-out view of a plenum of an extendable suction surface with compliant material disposed around an opening of the plenum so as to provide an enhanced seal when the suction surface is in contact with a bracing surface, utilizing aspects of the present invention.

To enhance its suction seal against a bracing surface, each plenum of the suction surface may also have a compliant seal composed of rubber or other flexible material that is disposed around its outer edge. For example, a material 900 is shown in FIG. 9 as being disposed around the edges of the plenum 521 of the suction surface 500. The compliant seal in this case may be in the form of a ring-shaped gasket conforming to the shape of the suction surface 500 with openings properly shaped and sized so as not to cover the openings of the plenums 521~524 when properly aligned on the suction surface 500.

Figure 10:
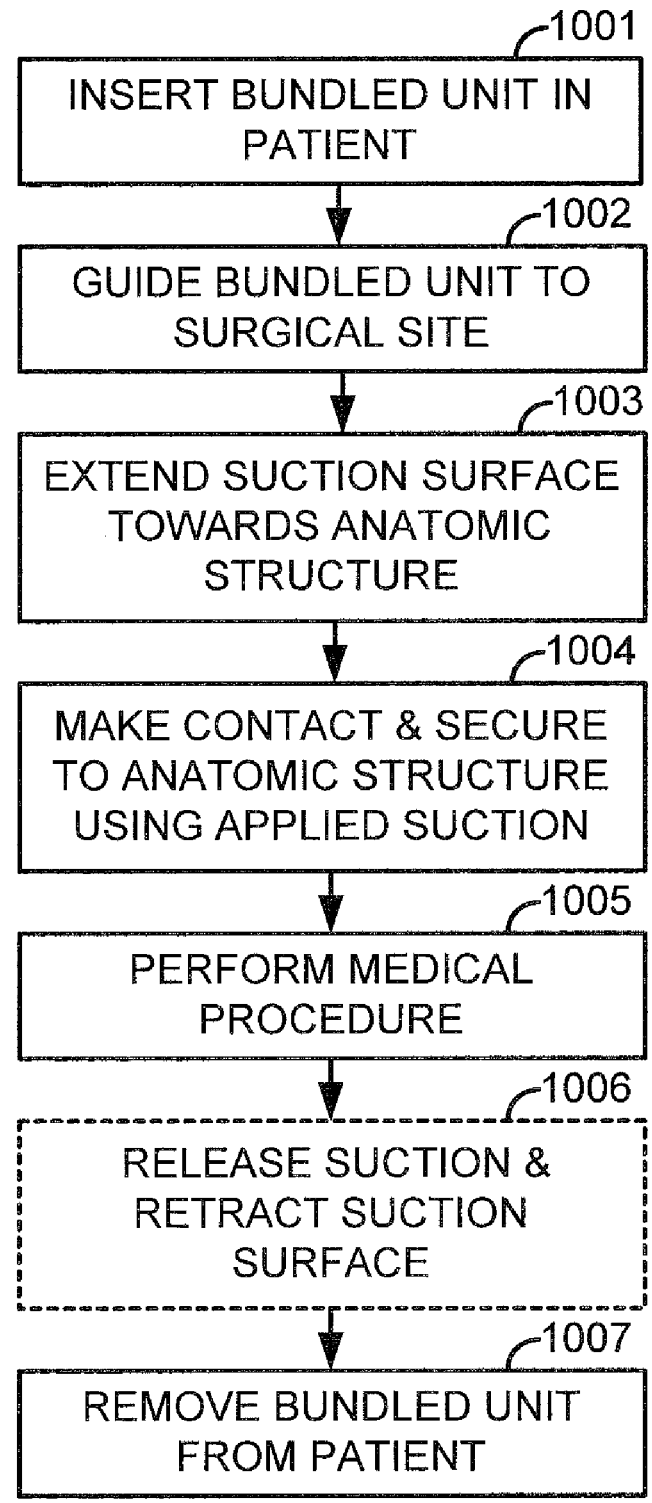
FIG. 10 illustrates a flow diagram of a method for performing a medical procedure at a surgical site within a patient using a bundled unit of medical devices having an extendable suction surface, utilizing aspects of the present invention.

FIG. 10 illustrates, as an example, a flow diagram of a method for performing a medical procedure at a surgical site within a patient using a bundled unit of medical devices (such as bundled unit 300) having an extendable suction surface (such as suction surface 500). In 1001, the bundled unit is inserted into the Patient through a single entry port such as a minimally invasive incision or a body lumen. In 1002, the bundled unit is robotically guided to a surgical site within the Patient using a robotic arm (such as the robotic arm 200).

In 1003, a suction surface (such as the suction surface 500) is extended away from the distal end of the bundled unit towards an anatomic structure at the surgical site until in 1004 contact with the anatomic structure is sensed. Sensing of the contact may be performed by any one of a number of techniques such as previously described in reference to FIG. 7. A vacuum source may be coupled to the suction surface, such as previously described in reference to FIGS. 4~5, before or after contact with the surface of the anatomic structure is sensed, so that when suction is applied and contact is made, the bundled unit is secured to the anatomic structure by the suction so as to brace the bundled unit against the anatomic structure.

In 1005, a medical procedure is then performed on target tissue at the surgical site using surgical tools (such as the surgical tools 338, 339) included in and extending out of the bundled unit while being viewed by an image capturing device (such as the image capturing device 340) also included in and extending out of the bundled unit, such as previously described in reference to FIGS. 1~7. The target tissue may be the anatomic structure to which the bundled unit has been braced in 1004.

In 1006, the suction may optionally be released and the suction surface retracted back to the distal end of the bundled unit prior to removing the bundled unit from the Patient in 1007. On the other hand, if the suction surface has been braced against the target tissue, the entire target tissue or a severed portion to which the suction surface has been secured to may be removed along with the bundled unit from the patient by maintaining the suction between the suction surface and the target tissue while robotically removing the bundled unit from the Patient in 1007.

Although the various aspects of the present invention have been described with respect to a preferred embodiment, it will be understood that the invention is entitled to full protection within the full scope of the appended claims.

I claim:

1. A medical unit comprising:
    an elongate structure;
    a first surgical tool extending through the elongate structure;
    a suction surface having a plurality of openings; and
    a plurality of tubes substantially evenly circumferentially spaced within and extending through the elongate structure, the plurality of tubes individually coupled at a distal end to the suction surface and couplable at a proximal end to an interface so that the suction surface is controllably extendable away from and retractable back to a distal end of the elongate structure in a straight-line path by extension and retraction of the plurality of tubes, the plurality of tubes individually having a conduit that is coupled at a distal end to a corresponding one of the plurality of openings of the suction surface and couplable at a proximal end to a vacuum source so that the plurality of openings of the suction surface is provided with a suction force capable of bracing the elongate structure against an anatomic structure within a patient when positioned so as to be in contact with the anatomic structure.

2. The medical unit according to claim 1, further comprising:
    a second surgical tool extending through the elongate structure.

3. The surgical instrument according to claim 2, further comprising:
    an image capturing device extending through the elongate structure.

4. The medical unit according to claim 1, wherein the plurality of openings are distributed on the suction surface so as to evenly apply suction forces to the suction surface.

5. The medical unit according to claim 4, wherein the suction surface comprises a ring structure having the plurality of openings forming one or more rings around a center of the ring structure.

6. The medical unit according to claim 5, further comprising:
    a second surgical tool extending through the elongate struture, wherein the first and second surgical tools each have an arm that is robotically extendable, rotatable and bendable so that end effectors of the first and second surgical tools may be manipulated to perform a medical procedure on the anatomic structure to which the suction surface is being braced against.

7. The medical unit according to claim 6, wherein the arms of the first and second surgical tools are manipulatable so that the end effectors of the first and second surgical tools are capable of operating on the anatomic structure both inside and outside of a central core of the ring structure.

8. The medical unit according to claim 1, wherein the plurality of tubes are individually semi-flexible so as to allow limited lateral movement of the suction surface when it is extended to a position away from the distal end of the elongate structure.

9. The medical unit according to claim 1, wherein the plurality of tubes are individually substantially rigid.

* * * * *